United States Patent [19]

Buelow

[11] Patent Number: 5,482,841
[45] Date of Patent: Jan. 9, 1996

[54] EVALUATION OF TRANSPLANT ACCEPTANCE

[75] Inventor: Roland Buelow, Palo Alto, Calif.

[73] Assignee: Sangstat Medical Corporation, Menlo Park, Calif.

[21] Appl. No.: 247,992

[22] Filed: May 24, 1994

[51] Int. Cl.$^6$ ............................................ G01N 33/543
[52] U.S. Cl. ................. 435/7.24; 435/7.95; 435/961; 435/962; 436/518
[58] Field of Search .................... 435/7.24, 7.95, 435/961, 962, 975; 436/518

[56] References Cited

U.S. PATENT DOCUMENTS

| | | | |
|---|---|---|---|
| 4,959,308 | 9/1990 | Ogden | 436/518 |
| 5,059,524 | 10/1991 | McKenzie et al. | 435/7.24 |
| 5,223,397 | 6/1993 | Pouletty | 435/7.24 |
| 5,270,169 | 12/1993 | Chang et al. | 435/7.24 |
| 5,292,641 | 3/1994 | Pouletty | 435/7.24 |

OTHER PUBLICATIONS

Davies et al., "Soluble HLA Antigens in the Circulation of Liver Graft Recipients", *Transplantation* 47(3):524–527 (1989).
Doxiadis and Gross–Wilde, "Typing for HLA Class I Gene Products Using Plasma as Source", *Vox Sang* 56:196–199 (1989).
Duquesnoy et al., "Multiscreen Serum Analysis of Highly Sensitized Renal Dialysis Patients for Antibodies Toward Public and Private Class I HLA Determinants", *Transplantation* 50(3):427–437 (1990).
Fauchet et al., "Occurrence and Specificity of Anti–B Lymphocyte Antibodies in Renal Allograft Recipients", *Transplantation* 30(2):114–117 (1989).
Fuller, "Monitoring HLA Alloimmunization", *Clinics in Laboratory Medicine* 11(3):551–570 (1991).
Gross–Wilde and Doxiadis, "Allotyping for HLA Class I Using Plasma as Antigen Source", *J. of Immunogenetics* 16:149–155 (1989).
Iwaki et al., "Successful Transplants Across T Warm–positive Crossmatches due to IgM Antibodies", *Clin. Transplantation* 2:81–84 (1988).
Martin et al., "Posttransplant Antidonor Lymphocytotoxic Antibody Production in Relation to Graft Outcoume", *Transplantation* 44(1):50–53 (1987).
Oldfather et al., "Prediction of Crossmatch Outcome in Highly Sensitized Dialysis Patients Based on the Identification of Serum HLA Antibodies", *Transplantation* 42(3):267–270 (1986).
Pouletty et al., "Typing of a Panel of Soluble HLA Class I Antigens by Enzyme–Linked Immunosorbent Assay", *Human Immunology* 40:000–000 (1994).
Stevenson et al., "Analysis of Soluble HLA Class II Antigenic Material in Patients with Immunological Diseases Using Monoclonal Antibodies", *J. of Immunological Methods* 86:187–190 (1986).
Talbot et al., "Rapid Detection of Low Levels of Donor Specific IgG by Flow Cytometry with Single and Dual Colour Fluorescence in Renal Transplantation", *J. of Immunological Methods* 112:279–283 (1988).
Takahashi et al., "Useful Antiglobulin Crossmatch Test for DST–Sensitized Patients", *Transplantation Proceedings* 19(1):794–799 (1987).
Terashita, "Flow Cytometry Crossmatching: An Update", in P. Terasaki (Ed.) *Clinical Transplants* pp. 391–396, (1989).
J. E. K. Hildreth, *Biochem. Jour.*, 207, 363–366, 1982.
M. Tanabe et al *Jour. Immunol.*, 148, 3202–3209, 1992.

*Primary Examiner*—David Saunders
*Attorney, Agent, or Firm*—Bertram I. Rowland; Bret E. Field

[57] ABSTRACT

Alloantigen is extracted from a cellular source, preferably blood cells, with a mild detergent, and partially purified by precipitation of potentially interfering components. The alloantigen preparation is then used in an assay to determine the presence and specificity of receptors specific for alloantigens. The detection of bound receptor is determined by ELISA or other suitable immunoassays.

13 Claims, No Drawings

EVALUATION OF TRANSPLANT ACCEPTANCE

TECHNICAL FIELD

The field of this invention is the detection of alloantigen specific receptors.

BACKGROUND

In many transplantation-type situations, there is concern for differences between the allotype, especially the HLA type, of a cell source and the cell recipient. Antibodies against alloantigens can be induced by multiple blood transfusions, pregnancy, or during a prior graft rejection. Although these antibodies may be low titer, and difficult to detect, their presence in the blood of a potential recipient is indicative that a new graft with matching alloantigens will be rejected. The determination of the presence and specificity of antibodies against foreign HLA antigens is therefore clinically important for monitoring transplant patients. Detection assays may test for reactivity against a panel of antigens, as an initial broad screen (panel reactive antibodies, PRA testing), or may be specific for a single donor (donor specific crossmatch).

The standard technique for HLA typing and detection of anti-HLA antibodies is microlymphotoxicity, where serum containing antibodies is incubated with HLA antigen-expressing lymphocytes, then with complement. In some cases anti-human immunoglobulin is added to augment cell killing. The level of cytotoxicity is estimated by discriminating between dead and viable cells using various dyes. This method has numerous disadvantages: it is labor intensive, time consuming, requires isolation of cells, requires viable cells, is nonspecific for HLA, and requires a subjective evaluation. Flow cytometry may also be used but requires a large number of cells and expensive instrumentation.

It is therefore of interest to provide alternative techniques which can be performed simply, can be automated, do not share the shortcomings described above, provide a readily discernible result which is significant for the prognosis of graft acceptance, and comparable to data from existing tests.

RELEVANT LITERATURE

References of interest include Duquesnoy et al. (1990) *Transplantation* 50: 427–37; Martin et al. (1987) *Transplantation* 44: 50–53; Grosse-Wilde et al. (1989) *J. Immunogenet.* 16: 149–55; Doxiadis and Grosse-Wilde (1989) *Vox Sang* 56: 196–99; Davies et al. (1989) *Transplantation* 47: 524–27; Stevenson et al. (1986) *J. Immunol. Methods* 86: 187–90; Fauchet et al. (1989) *Transplantation* 30: 114–129; Talbot et al. (1988) *J. Immunol. Methods* 112: 279–83; Iwaki et al. (1988) *Clin. Transplantation* 2: 81–84.

A review of alloantibody analysis may be found in Fuller (1991) *Clin Lab Med* 11:551–70; and Oldfather, et al. (1986) *Transplantation* 42:267–70. Terashita (1989) *Clin Transpl* 391–6 discusses the use of flow cytometry in crossmatch.

Methods of HLA typing have been previously described. U.S. Pat. No. 5,223,397 describes a method of determining HLA cross-match with a soluble form of HLA molecules found in biological samples. U.S. Pat. No. 5,292,641 describes the detection on a solid support of alloantigen or alloantigen specific antibodies. The use of the complement protein C1q bound to a solid substrate to detect HLA antigen-containing immune complexes is described in U.S. Pat. No. 5,270,169.

SUMMARY OF THE INVENTION

Reactivity between an alloantigen and an alloantigen-specific receptor is determined by combining an biological sample with alloantigen solublized from a cellular source with a mild detergent, and partially purified by precipitation of potentially interfering components. The alloantigen sample may be from one or a number of organ donors. The presence of bound receptor is determined by conventional immunoassay methods.

DESCRIPTION OF THE SPECIFIC EMBODIMENTS

Alloantigen is extracted from a cellular source, preferably blood cells, with a mild detergent, and partially purified by precipitation of potentially interfering components. The alloantigen preparation is then mixed with a biological sample of the alloantigen-specific receptor. The presence of bound receptor is determined by ELISA or other suitable immunoassays.

The subject invention finds particular utility in determining reactivity between an alloantigen and alloantigen-specific antibodies, which is indicative of immunological reactivity between two biological samples. An accurate assessment of the level and specificity of alloantibodies is critical for matching donor and recipient in tissue transplantation. Presence of specific alloantibodies for donor HLA is highly predictive that a graft will be rejected. Embodiments of this invention find use in identifying antibodies to known histocompatibility antigens (crossmatching), identifying histocompatibility antigens with antibodies of known specificities (tissue typing) and identifying general alloreactivity toward a number: of different histocompatibility antigens.

Detection of specific alloantibodies is made difficult by the generally high level of interfering background proteins and other biochemical macromolecules in blood. In particular, determination of HLA reactivity with soluble alloantigens from blood must overcome the background signal resulting from the high level of non-specific immunoglobulins present. The present invention utilizes a simple extraction and partial purification protocol which significantly reduces the amount of non-specific protein in the alloantigen sample. The accuracy of assay results is improved by the reduction in background noise.

An alloantigen is a direct or indirect product of an allele which may be detected as an antigen by another member of the same species. The products of such alleles include encoded polypeptides, but also specific polysaccharides and lipids synthesized by allele encoded enzymes. Alloantigens of particular interest in the present invention are histocompatibility antigens, which include major, known as HLA in human, and minor histocompatibility antigen groups.

By grafting it is meant that donor tissue is joined with the graft recipient's body. Preferred grafts include the transplantation of cells, tissues and organs. Of especial interest are the transfusion of blood or blood components, the grafting of bone, skin, bone marrow, etc., and the transplantation of tissues of the eye, pancreas, liver, kidney, heart, brain, bowel, lung, etc. Of greatest interest are transplantation of hematopoietic cells, e.g. bone marrow, mobilized hematopietic stem cells in peripheral blood, etc. and transplantation of kidneys. Such cells or tissues may be treated between collection and grafting. Pretreatment may include methods of fractionation to isolate or enhance or decrease the concentration of specific cell types, tissue components, compounds, etc. In addition, donor tissue or cells may be subject to in vitro treatments such as culture, differentiation, proliferation, and genetic manipulation prior to transfer to the recipient.

As used herein, a graft recipient is an individual to whom tissue or cells from another individual (donor), generally of the same species, has been transferred. The graft recipient and donor are generally mammals, preferably human. The stage of development of the recipient will generally range from fetal to adult, usually from juvenile to adult.

In most cases, the potential graft recipient will be the source of the biological sample which contains the alloantibodies to be assayed. The biological sample will generally be blood derived, usually in the form of plasma or serum. In most cases the serum will be diluted at least about 1:10, usually about 1:100 and not more than 1:1000. Any physiological buffer may be used, e.g. PBS, normal saline, HBSS, dPBS, etc. Dilution is often useful to reduce the level of background signal, but the titer of alloantibodies is often low, and so substantial dilution beyond the levels indicated will not usually be performed.

The source of alloantigen may be a potential tissue donor, or a broad panel of samples. The donor may be of any stage of development from embryo to adult. Donor tissue may also be extracted from deceased individuals where the tissue is viable at the time of grafting. The cellular sources for alloantigen include blood, tissue biopsy samples, in particular, kidney, skin, lung, heart, bone marrow, etc.; organ or tissue culture cells; and the like. Also included in the term are derivatives and fractions. Preferred sources are blood and the buffy coat fraction of blood, which is a concentrated source of leukocytes, and therefore HLA alloantigens.

Membrane bound alloantigen is extracted from cells with a mild detergent, particularly non-ionic or zwitterionic detergents. The detergent must be compatible with the precipitating agent used in a partial purification step, ie. the detergent will not precipitate with addition of the agent. Non-ionic alkylated sugar detergents, e.g. n-decyl β-D-glucopyranoside, n-dodecyl β-D-glucopyranoside, n-dodecyl β-D-maltoside, n-heptyl β-D-glucopyranoside, n-octyl β-D-glucopyranoside, n-octyl α-D-glucopyranoside, n-nonyl β-D-glucopyranoside, etc. are useful for selective extraction of HLA antigens. A preferred detergent is n-octyl β-D-glucopyranoside. The detergent will be used at a concentration of at least 1%, more usually about 4%, and not more than 10%, usually not more than 5%. The concentration of detergent must be sufficient to solubilize alloantigen from the cell membrane, which can be verified by gel electrophoresis of supernatant samples.

The solution comprising extracted alloantigen, detergent and cells may be centrifuged at this point to get rid of large particles, e.g. cells, or more often, can be directly used in the next step. A precipitating agent is added to the solution, which is then incubated for a period of time sufficient to aggregate interfering background components. Such background components will typically be proteins, particularly immunoglobulins, membrane fragments, and other large biomolecules. Normally the incubation will be for at least about 5 minutes, more usually for at least about 10 minutes, in some cases for about 1 hour, and usually not more than 3 hours. Useful agents for precipitation are polyethylene glycol and ammonium sulfate. Ammonium sulfate is used at a concentration of at least about 30%, more usually about 40%, and not more than about 80%, usually not more than about 50%. The concentration of precipitating agent is critical to the invention. It must be sufficient to precipitate background components such as immunoglobulin, but not be at such a high concentration that the alloantigen will be precipitated. The procedure can be verified by gel electrophoresis to analyze the relative concentration of alloantigen vs. background proteins. The sample is then centrifuged, and the pelleted debris discarded. The remaining supernatant is used as the source of alloantigen in an immunoassay with the receptor sample.

Measuring the concentration of alloantigen-specific receptor may be accomplished by a variety of specific assays. In a preferred embodiment, an ELISA sandwich type assay is used, similar to conventional immunoassays for cross-match or PRA testing. A sandwich assay is performed by first attaching a capture agent specific for the alloantigen to a solid support. The capture agent may be bound to the surface by any convenient means, depending upon the nature of the surface. The particular manner of binding is not crucial so long as it is compatible with the other reagents and overall methods of the invention. Where the capture agent is antibody, it may be bound to the plates covalently or non-covalently, preferably non-covalently.

Especially useful capture agents are antibodies against the alloantigen. Instead of whole or intact antibodies, one may use antibody fragments, e.g., Fab, F(ab')$_2$, light or heavy chain fragments, etc. The use of affinity purified polyclonal antibodies or monoclonal antibodies is preferred. Immune molecules with alloantigen binding affinity such as CD4, CD8, and T cell receptors may also provide useful capture agents, either directly or through derivatives thereof. Lectins may be useful where the alloantigen can be selected by the presence of saccharides.

In a preferred embodiment of the invention, the capture agents are antibodies specific to one or more HLA alloantigens. Such antibodies may be polyclonal or monoclonal and are generally commercially available or alternatively, readily produced by techniques known to those skilled in the art. For detecting Class II HLA molecules, the antibodies may be specific for either α or β chains; for Class I HLA, specificity may be to the MHC gene encoded chain, particularly the α3 domain or the associated β-2 microglobulin chain; or for either Class, specificity may be to a conformational epitope expressed by the combination of both chains. The antibodies may be specific to epitopes conserved across a class of HLA molecules or specific to an epitope expressed by a subset of HLA molecules. Subsets of Class II molecules include products of the DP, DQ and DR gene regions and those of Class I molecules include products of the A, B and C regions. The antibodies may be directed to a constant region or a portion of the polymorphic region of specific alleles.

The insoluble supports may be any compositions to which capture agents can be bound, which is readily separated from soluble material, and which is otherwise compatible with the overall method. The surface of such supports may be solid or porous and of any convenient shape. Examples of suitable insoluble supports to which the receptor is bound include beads, membranes and microtiter plates. These are typically made of glass, plastic (e.g. polystyrene), polysacharides, nylon or nitrocellulose. Microtiter plates are especially convenient because a large number of assays can be carried out simultaneously, using small amounts of reagents and samples. Where separations are made by magnetism, the support generally includes paramagnetic components, preferably surrounded by plastic.

Before adding alloantigen samples, the non-specific binding sites on the insoluble support i.e. those not occupied by capture agent, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Sample supernatants containing the solubilized alloantigen are then added to separately assayable supports (for example, separate wells of a microtiter plate) containing support-bound capture agent. In an example of HLA crossmatch, an alloantigen sample from a prospective tissue donor is bound to the solid support through a specific capture agent, and serum from the prospective tissue recipient is assayed for the presence of specific antibodies. In another example, a series of different donor samples are used in separate sample aliquots that are then assayed in parallel for the presence of respective HLA-specific antibodies.

Generally from about 0.001 to 1 ml of solubilized alloantigen, diluted or otherwise, is sufficient, usually about 0.01 ml sufficing. Preferably, each supernatant will be added to multiple wells so that mean values can be obtained. The incubation time should be sufficient for alloantigen molecules to bind the capture agent. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a biological sample containing the alloantigen-specific receptor is applied. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Preferred are physiological samples such as blood or derivatives thereof, such as serum or plasma (hereafter "blood"). Such samples will generally be complex mixtures, where the concentration of specific receptor is low.

Particular receptors of interest are antibodies. The isotypes IgG and IgM will be found in blood, IgA may be detected in secreted fluids, e.g. saliva, etc. Other receptors which may be indicative of an immune response are T-cell receptors. Of particular interest are alloantibodies found in the serum of transplant or prospective transplant patients. The volume, composition and concentration of the biological sample provides for measurable binding to the alloantigen already bound to the capture agent. The volume will be from about 0.1 µl to 1 ml is sufficient, usually about 1 µl sufficing. The incubation time should be sufficient for the receptor to bind available bound alloantigen molecules. Generally, from about 0.1 to 3 hr is sufficient, usually 1 hr sufficing.

After the receptor has bound the alloantigen, the insoluble support is generally again washed free of non-specifically bound proteins, essentially as described for prior washes. The presence of bound alloantigen-specific receptor is detected with a labeled reagent, particularly anti-human antibodies, e.g. antisera. Examples of labels which permit direct measurement of receptor binding include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the labeled reagents are antibodies, preferably labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is o-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate o-phenylenediamine for example, light absorbance at 490–495 nm is conveniently measured with a spectrophotometer.

The samples will be run with positive and negative controls to provide reference values. The negative controls will have a solid substrate prepared and detected by the same procedure, but will lack alloantigen or receptor analyte. The negative controls must be below a pre-determined cutoff value, which can be determined empirically.

A positive control will be performed using a reagent which will bind to the bound alloantigen. A convenient positive control for detecting the presence of antibodies to HLA Class I antigens is provided by adding to bound alloantigen a known amount of an antibody which reacts with human $\beta_2$-microglobulin, an invarient chain found with all HLA Class I proteins. The antibody may be directly conjugated to a label which allows for detection, or may be used in combination with second antibody, particularly the labeled detector reagent used in the test samples. The positive control should fall within a pre-determined range, based on what would be expected for the known amount of allele present.

The cutoff value used in the assay will be empirically determined by collecting data from a large number of samples, and calculating a cutoff value which optimizes the agreement between the subject assay and the conventional assay, microlymphocytoxicity.

A device which may find application with the subject invention is one having a porous substrate to which the capture agent is bound. Supporting the substrate is an absorbent layer which will absorb the various fluids, including samples and washes. Desirably, the absorbent layer and porous layer are separated by a flow control film, having a plurality of orifices which direct the rate and direction of flow through the porous layer. For further description of this device, see U.S. Pat. No. 5,147,780 issued Sep. 15, 1992. This device, as well as comparable devices allow for the simultaneous determination of a plurality of samples, either from different sources, or at different concentrations from the same source. Thus, one can carry out a plurality of determinations at the same time. Alternatively, microtiter plates may be employed where the bottoms of the wells are porous to allow for filtration. The particular device which is employed will depend upon the number of samples to be determined, available equipment, and the like.

The following examples are offered by way of illustration and not by way of limitation.

EXPERIMENTAL

Example I. Crossmatch ELISA

Preparation of plate and reagents

Nunc Maxisorb plates were coated with an anti-HLA class I monoclonal antibody (anti-alph 3). The coating solution was 10 μg/ml of F(ab)'$_2$-TP25 in 0.1M Na Acetate. Each well was coated with 100 μl of coating solution and incubated for 6±0.5 hours at 25° C.,≧98% relative humidity. At the end of incubation the coating solution was aspirated and the wells were rinsed once with 50 mM phosphate buffer at 300 μl/well. Then the wells were blocked with PRA block solution (SangStat Medical Corp) at 300 μl/well for 18±4 hours at 25° C.,>98% relative humidity. At the end of incubation the blocking solution was aspirated and the plates were washed once with 50 mM phosphate buffer at 300 μl/well. Then the plates were coated with 4% sucrose solution at 300 μl/well for 10 minutes. The sucrose solution was aspirated from all the wells. The plates were dried in a drying tunnel for 7 minutes at 52° C. The plates were bagged with desiccants and stored at 4° C. for future use.

Donor blood preparation

Fresh blood from 20 random donors, approximately 20 ml each, from Stanford Blood Center were collected for this study. The blood contained the anticoagulant ACD. Each donor blood was treated as follows:

Whole blood—The required volume of donor blood was measured and put into polypropylene tubes. A stock solution of 20% n-octyl β-D-glucopyranoside (OG) in PBS was added to the blood to give a 2% weight/volume final concentration. The donor blood and OG were mixed well and incubated for 10 minutes at room temperature. Then saturated ammonium sulfate (SAS) was added to the blood and OG mixture to give a final concentration of 40% ammonium sulfate weight/volume. The donor blood, OG and SAS were mixed very well by vortexing and incubated at room temperature for 10 minutes. Then the mixture was centrifuged at 15,000 g in the microfuge for 5 minutes. The supernatant was recovered, transferred into clean polypropylene tubes and centrifuged again for 3–5 minutes. The supernatant was diluted immediately 1:4 in 50 mM phosphate buffer, 0.01% thimerosal pH 7.4.

Buffy coat—Donor blood was spun at 1500 rpm, 4° C. for 10 minutes in a Beckman TJ-6 centrifuge. The buffy coat with plasma was carefully collected and put into polypropylene tubes. Some red cells may be taken together with the buffy coat. The required volume of buffy coat was measured and treated with OG and SAS exactly the same way as with whole blood except the supernatant was diluted 1:3 in the buffer.

Recipient serum preparation

Thirteen recipient sera of known % PRA values from 0 to 100% (by PRA-STAT and lymphocytotoxicity) were selected for this study. Each recipient serum was diluted 1:101 in PRA 1X Specimen Diluent (SangStat Medical Corp).

Conjugate

Horse radish peroxidase (HRP) conjugate of goat anti-human IgG-Fc was diluted 1:8,000 in PRA 1X Specimen Diluent.

Substrate

OPD (o-phenylenediamine) solution was prepared fresh prior to use within 15 minutes at 3 mg/ml in the Substrate Buffer.

Assay Protocol

Diluted donor supernatant from OG/SAS treated whole blood or buffy coat was pipetted into each test well and donor-only well, 100 μl/well. 50 mM phosphate buffer, 0.01.% thimerosal pH7.4 was added into each recipient-only well, 100 μl/well. The plate was covered with plastic sealer and incubated at 37° C. for one hour.

The plate was aspirated and washed 3 times with PRA wash buffer, 325 μl/well each time.

Diluted recipient serum was pipitted into both test and recipient-only wells, 100 μl/well. 1×PRA specimen diluent was pipetted into donor-only well, 100 μl/well. The plate was incubated at 37° C. for one hour.

The plate was aspirated and washed 3 times with PRA wash buffer, 325 μl/well each time.

Diluted goat anti-human IgG Fc-HRP conjugate was pipetted into all wells. The plate was incubated at room temperature for one hour.

The plate was aspirated and washed 3 times with PRA wash buffer, 325 μl/well each time.

OPD substrate solution was pipetted into all wells. The plate was incubated for 7 minutes at room temperature.

Stop solution was added into all wells, 100 μl/well.

The plate was read in a microplate reader at a wavelength of 492 nm and 600 nm reference wavelength.

Interpretation of Assay Results

For each donor and recipient pair the crossmatch ratio was calculated as: Ratio=O.D. of test well/(O.D. of donor-only+ recipient-only wells) Each O.D. was the mean value of duplicate wells.

Each crossmatch ratio was compared with a cut-off value.

If the crossmatch ratio was≧cut-off value, the recipient serum contained IgG antibodies to the HLA antigens in the donor. This was a positive result.

If crossmatch ration was<cut-off value, the recipient serum was negative for IgG antibodies to the HLA antigens in the donor.

To compare results with microlymphocytoxicity, the following equations were used:

True positives (TP) are samples which are positive by both microlymphocytoxicity and ELISA.

True negatives (TN) are samples which are negative by both microlymphocytoxicity and ELISA.

False positives (FP) are samples which are negative by microlymphocytoxicity and positive by ELISA.

False negatives (FN) are samples which are positive by microlymphocytoxicity and negative by ELISA.

$$Agreement = \frac{TP + TN}{TP + TN + FP + FN}$$

$$Specificity = \frac{TN}{TN + TP}$$

$$Sensitivity = \frac{TP}{TP + FN}$$

Lymphocytoxicity assay

Peripheral blood lymphocytes (PBL) were isolated from fresh donor blood by a Ficoll-Hypaque technique. The concentration of PBL was adjusted to 2.0–2.5 million cells per ml. On a Terasaki tray one μl of recipient serum (untreated and DTT treated) and one μl of donor PBL were incubated for 45 minutes at room temperature. Then 5 μl of rabbit complement was added into all wells, and incubated for 90 minutes at room temperature. Finally, 10 μl Stain Fix was added to all wells. Cell lysis was scored under the phase contrast microscope. A positive reaction was defined as 25% cell lysis above the negative control. Autocrossmatch was always included in the assay.

Results Comparison between crossmatch ELISA and lymphocytotoxicity

A total of 260 crossmatch samples from 20 donors and 13 recipients were tested. The results of crossmatch ELISA were compared with lymphocytotoxicity assay. Using donor's whole blood preparation in the crossmatch ELISA, and a cut-off value of 2.2, the values shown in Table 1 were obtained.

TABLE 1

| E L I S A | | Lymphocytotoxicity | | |
|---|---|---|---|---|
| | | Positive | Negative | |
| | Positive | 77 | 22 | |
| | Negative | 18 | 143 | |
| | | 95 | 165 | 260 |

The agreement between crossmatch ELISA and lymphocytotoxicity results was 84.6%, the specificity 86.6% and the sensitivity 81.0%.

Using donor's buffy coat preparation in the crossmatch ELISA and a cutoff value of 2.5, the values shown in Table 2 were obtained.

TABLE 2

| E L I S A | | Lymphocytotoxicity | | |
|---|---|---|---|---|
| | | Positive | Negative | |
| | Positive | 91 | 18 | |
| | Negative | 5 | 146 | |
| | | 96 | 164 | 260 |

The agreement between ELISA and lymphocytotoxicity results was 91.1%, the specificity 89.0% and the sensitivity 89.0%.

We therefore conclude that the subject methods provide a simple accurate diagnostic assay for determining HLA crossmatch and PRA. The results are comparable to lymphocytoxicity assays, but provide benefits in the speed, ease and automation with which the assay can be performed. The level of background signal is reduced when compared to similar assay systems.

It is evident from the above results, that the subject method provides an easy procedure for determining HLA reactivity. The method is rapid, easily performed, requires readily available reagents, and can be performed with numerous samples determining numerous alleles in a highly efficient manner.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of at least one receptor analyte specific for an HLA antigen in a biological sample, said method comprising:

treating at least one cellular source of HLA antigens with a non-ionic or zwitterionic detergent to provide a solution comprising solubilized HLA antigens;

precipitating out interfering background components from said solution by combining said solution comprising solubilized HLA antigens with a precipitating agent at a concentration sufficient to precipitate said interfering background components but not sufficient to precipitate said solubilized HLA antigens;

binding said HLA antigens to a solid support;

adding said biological sample to said solid support; and detecting the presence of said at least one receptor to said HLA antigen present on said support by means of a detectable signal as compared to a cut-off value, wherein a difference in signal between said detectable signal and said cut-off value is indicative of the presence of said receptor.

2. A method according to claim 1, wherein said detergent is a non-ionic alkylated sugar detergent.

3. A method according to claim 2, wherein said non-ionic alkylated sugar detergent is n-octyl β-D-glucopyranoside.

4. A method according to claim 1, wherein said precipitating agent is ammonium sulfate and said precipitating out interfering background components further comprises the steps of:

incubating said solution for a period of time sufficient to aggregate said interfering background components;

centrifuging said solution; and isolating supernatant.

5. A method according to claim 4, wherein said receptor is alloantibody and said biological sample is blood, and wherein said detecting comprises:

washing said solid support substantially free of non-specifically bound protein;

adding a labeled reagent capable of binding to said alloantibody; and detecting the presence of said labeled reagent bound to said support.

6. A method according to claim 5, wherein said labeled reagent is enzyme labeled anti-human antibody.

7. A method according to claim 5, wherein said labeled reagent is a fluorochrome labeled anti-human antibody.

8. A method according to claim 4, wherein said at least one cellular source of HLA antigens is selected from the group consisting of blood and the buffy coat fraction of blood.

9. A method according to claim 8 wherein said at least one cellular source of HLA antigens provides a panel of HLA allotypes.

10. A method according to claim 8 wherein said cellular source of HLA antigens is a prospective tissue donor for transplantation, and said biological sample is blood from a prospective tissue recipient.

11. A method for performing HLA cross-match by detecting the presence or absence of alloantibodies specific for at least one HLA antigen in a blood sample from a prospective tissue recipient, wherein the absence of alloantibodies is indicative of an HLA cross-match, said method comprising:

treating a cellular source of HLA antigens, selected from the group consisting of blood and the buffy coat fraction of blood, taken from a prospective donor, with n-octyl β-D-glucopyranoside to provide a solution comprising HLA antigens;

adding ammonium sulfate to said solution;

incubating said solution for a period of time sufficient to aggregate interfering background components;

centrifuging said solution;

isolating supernatant from said centrifuged solution;

binding said HLA antigens present in said supernatant to a solid support;

adding said blood sample to said solid support; and washing said solid support substantially free of non-specifically bound protein;

adding a labeled reagent capable of binding to said alloantibodies; and detecting the presence of said labeled reagent bound to said support by means of a detectable signal as compared to a cut-off value, wherein the difference in signal between said detectable signal and said cut-off value is indicative of the presence of said alloantibodies.

12. A kit for use in a method for detecting the presence of at least one receptor analyte specific for an HLA antigen in a biological sample, said kit comprising:

a solid support coated with a capture agent capable of specifically binding to a conserved region of a subset of interest of HLA antigens;

n-octyl β-D-glucopyranoside;

a precipitating agent selected from the group of polyethylene glycol and ammonium sulfate; and a labeled reagent which specifically binds to human antibodies.

13. A kit according to claim 12, wherein said capture agent is antibody directed to the α3 domain of HLA Class I heavy chain.

* * * * *